United States Patent [19]

Evans

[11] Patent Number: 4,645,491
[45] Date of Patent: Feb. 24, 1987

[54] SURGICAL NEEDLE

[76] Inventor: David Evans, 16 Wells Hill Ave., Toronto, Ontario, Canada, M5R 3A6

[21] Appl. No.: 708,634

[22] Filed: Mar. 6, 1985

[30] Foreign Application Priority Data

Mar. 9, 1984 [CA] Canada ................................. 449239

[51] Int. Cl.$^4$ ............................................. A61M 5/18
[52] U.S. Cl. .................................... 604/158; 604/161; 604/53; 604/117; 604/273; 128/DIG. 18
[58] Field of Search ............... 604/158, 161, 159, 160, 604/162, 163, 51–53, 117, 168, 272–274, 500, 164; 128/DIG. 18

[56] References Cited

U.S. PATENT DOCUMENTS

| | | | |
|---|---|---|---|
| 3,703,174 | 11/1972 | Smith | 604/159 |
| 3,835,854 | 9/1974 | Jewett | 604/160 |
| 4,054,136 | 10/1977 | Von Zeppelin | 604/160 |
| 4,194,509 | 3/1980 | Pickering et al. | 604/111 |
| 4,292,970 | 10/1981 | Hession, Jr. | 604/158 |
| 4,333,455 | 6/1982 | Bodicky | 604/158 |
| 4,354,491 | 10/1982 | Marbry | 604/160 |
| 4,363,176 | 1/1986 | Gustavsson et al. | 604/163 |
| 4,471,778 | 9/1984 | Toye | 604/160 |
| 4,556,059 | 12/1985 | Adamson, Jr. | 604/161 |

FOREIGN PATENT DOCUMENTS

| | | | |
|---|---|---|---|
| 1483989 | 6/1967 | France | 604/163 |
| 1381053 | 1/1975 | United Kingdom | 604/160 |

Primary Examiner—Stephen C. Pellegrino
Assistant Examiner—Mark Rooney
Attorney, Agent, or Firm—Merchant, Gould, Smith, Edell, Welter & Schmidt

[57] ABSTRACT

The invention provides a catheter placement apparatus for use in inserting a catheter to a preferred depth, the device comprising a surgical needle with a longitudinal window through which a catheter inserted into the needle can be viewed, and a catheter having a colored patch of the same length as the window and a series of spaced, visually distinct markings, proximal to the patch. The position of the catheter can be accurately located by aligning the colored patch with the window and then inserting the catheter until at least one mark appears in the window, recording the distance of a mark from the surface of the skin and using this recorded distance to relocate the catheter, if necessary.

13 Claims, 4 Drawing Figures

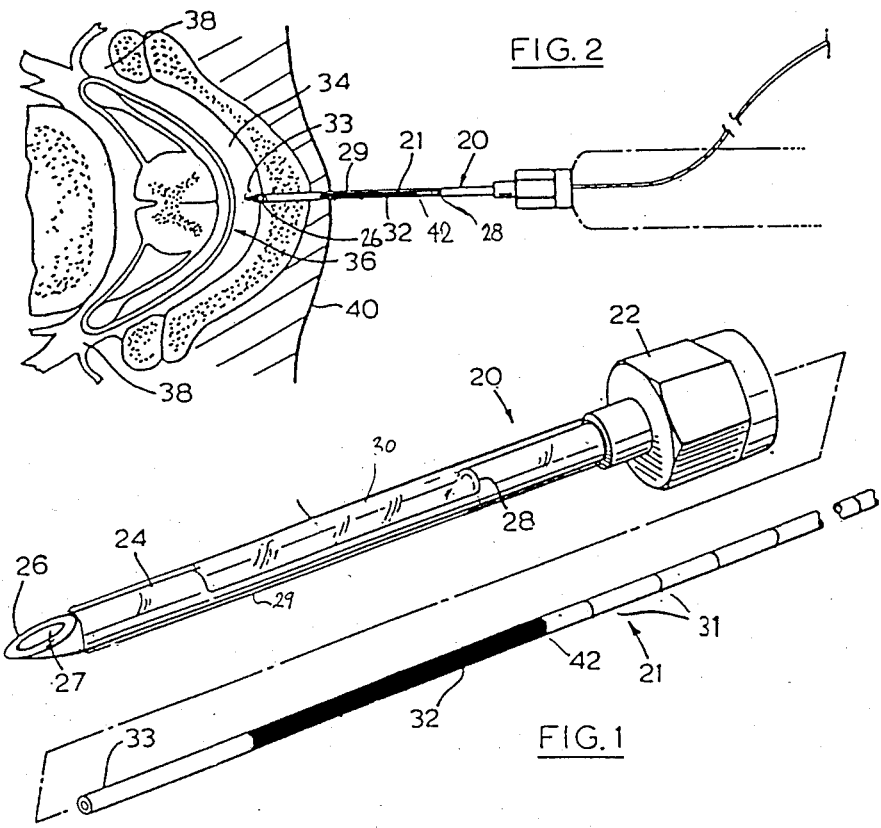
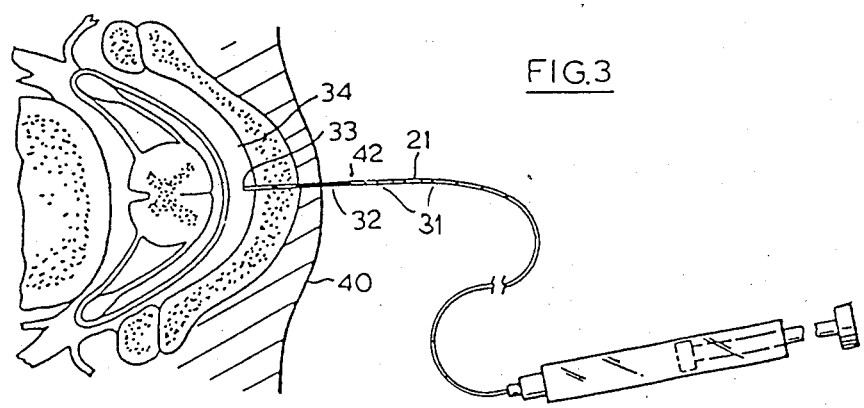

4,645,491

SURGICAL NEEDLE

This invention relates to a catheter placement apparatus having a catheter which can be inserted to a preferred depth in medical procedures such as providing peridural block injections.

It is known that in such medical procedures, the leading end of the catheter should be confined to a predetermined depth. For instance, in peridural block injections the catheter should be confined to the peridural space adjacent the spine without bending the catheter excessively which would collapse the catheter locally. It is therefore important that the catheter be inserted and maintained at a controlled depth.

For the purposes of describing the invention and to exemplify its use, this description will be concerned with catheter placement in peridural block injections.

Present catheter placement apparatus include an apparatus having a surgical needle and a catheter which can be moved through the needle into position. In peridural block injections, because the peridural space has a negative pressure, a droplet of water can be placed at the inlet end of the needle so that when the needle is inserted into the peridural space, the droplet of water is drawn down the needle. This water movement indicates that the needle has reached the preferred depth. The catheter is then slid inwardly through the needle until a mark on the catheter reaches the outer end of the needle. The mark is positioned to indicate that the leading end of the catheter is about to pass out of the open tip of the needle. Consequently, the catheter can then be slid a small distance further inwardly in order to have a positive displacement into the peridural space. Next the needle is withdrawn over the catheter leaving the catheter inserted. The catheter tends to move when the needle is removed and at that point, there is no way of checking that the catheter is still properly inserted in the peridural space. If the catheter has moved, it is very difficult to correct the position of the catheter without forcing the leading end of the catheter out of the peridural space or bending the catheter to the extent of collapsing it locally.

It is the purpose of the present invention to provide a catheter placement apparatus which will enable the operator to check that a catheter has been properly placed after the needle has been withdrawn. Accordingly, a catheter placement apparatus is devised which comprises a catheter having a series of markings thereon, in combination with a surgical needle through which the catheter can be inserted and which includes a window for viewing the markings on the catheter to enable the operator, while the needle is in place, to note a reference point on the catheter relative to the patient's outer skin for ensuring that the desired placement has been maintained after the needle has been removed.

In a preferred embodiment of the invention the needle is covered with a heat shrinkable transparent plastic and the catheter has a coloured patch which fills the slot when the catheter tip is at the needle tip, and when the catheter is inserted further the edge of the patch appears, then the series of spaced markings.

The invention will be better understood with reference to the drawings, in which:

FIG. 1 is a perspective view of portions of a surgical needle and a catheter forming parts of a preferred embodiment of a catheter placement apparatus according to the invention;

FIG. 2 is a sectional plan view of the relevant portion of a patient's back showing the use of the placement apparatus for peridural block injections;

FIG. 3 is a view similar to FIG. 2 and further illustrating the use of the placement apparatus after removal of the surgical needle.

Figure 4:
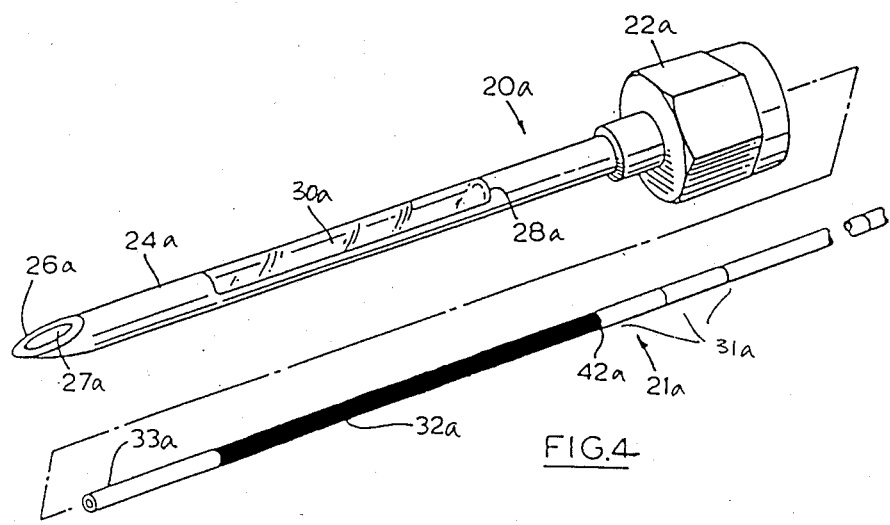
FIG. 4 is a view similar to FIG. 1 of an alternative embodiment of placement apparatus according to the invention.

Reference is made initially to FIG. 1. The preferred embodiment of the present invention includes a surgical needle 20 and a flexible catheter 21 which can be slidably inserted into the needle as indicated. The needle 20 has a head portion 22 and an elongated hollow stem portion 24 of uniform inner and outer diameters. A leading end 26 of the needle 20 is formed to provide a sharp edge around an outlet 27 and a longitudinal slot 28 is formed in the stem portion 24. The slot is covered by a thin-walled transparent polytetrafluoroethylene (PTFE) tube 29 which is heat shrunk over the stem portion 24 of the needle 20. This tube effectively forms a window 30 over the slot 28. Although the thickness of the tube increases the effective diameter of the stem portion 24, the tube 29 is so thin that it does not appreciably increase the overall diameter of the needle 20. Also because the tube is of PTFE, the surface friction of the needle is reduced to facilitate insertion.

The preferred embodiment of the present invention also includes the thin-walled hollow catheter 21 made of inert, flexible, polytetrafluoroethylene (PTFE). The catheter 21 is substantially of uniform inner and outer diameters throughout its length, its outer diameter being smaller than the inner diameter of the surgical needle 20 to facilitate passage of the catheter 21 through the needle 20. The catheter is coloured with a black patch 32 which is the same length as the longitudinal slot so that, when a leading end 33 of the catheter is inserted adjacent the leading end 26 of the needle 20, the black portion 32 is coincident with the longitudinal slot 28 and can be viewed through the window 30. Circular bands 31 are also provided on the catheter spaced 1 cm. along the catheter between the proximal end and the black patch 32. Each band is distinguished from other bands by its colour. The patch and the bands 31 are marked on the catheter 21 using non-reactive vegetable dyes.

Reference is now made to FIG. 2 which shows the preferred embodiment of the catheter placement apparatus inserted in a patient's back during catheter placement procedure. For effective results, it is intended that the leading end 33 of the catheter 21 be located in the peridural space 34 adjacent the spinal area 36. If advanced too far, the catheter 21 may either leave the peridural space 34 and go into the outer area 38 or become twisted and bent thereby restricting passage through the catheter. This is undesirable because it reduces the effectiveness of the injection. To locate the catheter 21, a droplet of water is first placed in the head portion 22 of the needle 20 just prior to insertion. Next the needle 20 is inserted through the patient's back in the area of the lower spine until the tip of the needle enters the peridural space 34. Because this space has a negative pressure, the droplet of water is drawn down the stem portion 24 of the needle 20 thereby indicating the position of the needle tip. Once the needle 20 is properly located in the peridural space 34, part of the window 30 will be visible outside the patient's skin 40 depending on the amount of flesh through which the needle has had to pass. The catheter 21 is then slid through the needle 20 until the black portion 32 coincides with the longitudinal slot 28, thus indicating to the operator that the leading end 33 of the catheter 21 has reached the end of the needle 20. The catheter is then advanced a short distance to ensure a positive displacement of the end 33 into the peridural space 34. When this occurs the proximal end 42 of the black portion will be visible through the window 30 with one or more of the circular bands 31. Of the bands 31 visible in the window 30, the colour and the distance of the band nearest to the patient's skin 40 is noted. The needle 20 is withdrawn by sliding it along and off the catheter 21 leaving the catheter in place as shown in FIG. 3. Some movement of the catheter is inevitable. However, the catheter position may be checked using the position of the coloured band noted earlier in the window 30. The catheter is moved until the same band is positioned the same distance from the skin 40 when it was viewed in the needle window 30. (See FIG. 3) The coloured band and its position relative to the skin 40 can be recorded for later reference to ensure that the catheter remains in the proper location throughout the injection period.

It will be appreciated from the foregoing that the invention can take many forms consistent with utilizing a viewing window in the surgical needle used for insertion and a series of marks on the catheter.

In an alternative embodiment shown in FIG. 4, and in which like numerals denote like parts with the suffix "a" added, the slot 28a could be filled by a transparent material, such as plastic, forming a window 30a which lies flush with the stem portion so that the stem diameter remains substantially unchanged. Also the black patch may be replaced by more bands of different colours. However the black patch gives a clear and rapid indication when the window is filled that the catheter end has reached the end of the needle and for these reasons is preferred.

Other transparent material could be used insted of PTFE for the shrink-wrapping and the catheter black patch may be any colour which, when viewed through the window, indicates that the catheter's leading end has reached the end of the needle. Other forms of bands 31 can be utilized. For instance, spaced marks of increasing width, or a series of spaced marks consisting of one or more encircling lines, each mark containing a number of lines one greater than the mark before it.

These variations are typical of alternative embodiments of the invention which fall within the scope of the invention described and claimed.

I claim:

1. Apparatus for use in accurately locating a catheter with respect to the outer surface of a patient's skin, the apparatus comprising:
    a hollow surgical needle having an elongate stem portion of uniform inner and outer diameters defining a sharpened leading end and an opening at that end, a window formed through a portion of said stem with means for providing airtight separation between an interior of said stem visible through said window and an exterior of said stem, said window being of sufficient longitudinal extent that a part of this portion will be inserted into the patient's skin when the needle is inserted to a required depth;
    a flexible tubular catheter adapted to be slidably inserted in the hollow surgical needle and moveable through the needle to project out beyond said opening in the leading end of the needle, the catheter including a leading end and markings spaced along its length including a first marking which cooperates with said window to indicate alignment of said leading edge of said needle and said leading edge of said catheter;
    whereby said needles can be inserted to a required depth and the leading end of the catheter can be inserted into and through the needle to a desired position with said first marking and said location indicating said alignment and with the markings being visible through the window, the markings being used as a guide to indicate the amount of catheter entered into the needle and so that one of the markings visible through the window can be used as a reference point to permit the catheter to be located in the same position relative to the skin surface after the needle has been removed.

2. Apparatus as claimed in claim 1 wherein the window is a longitudinal slot formed in the stem portion and said means for providing airtight separation comprises a thin transparent material, covering the slot in airtight engagement.

3. Apparatus as claimed in claim 1 wherein the window is a longitudinal slot formed in said stem portion and said means for providing airtight separation comprises a transparent material fitted in the slot so that the outer surface of the window is substantially flush with the surface of the stem portion with said material joined to said stem in airtight engagement.

4. Apparatus as claimed in claim 2 wherein the catheter has a coloured patch comprising said first marking which is of substantially the same length as the longitudinal slot, the patch being positioned on the catheter so that when the catheter is inserted into the needle, with all of the patch showing in the window, the catheter has its end at the end of the needle.

5. Apparatus as claimed in claim 3 wherein the catheter has a coloured patch comprising said first marking which is of substantially the same length as the longitudinal slot, the patch being positioned on the catheter so that when the catheter is inserted into the needle, with all of the patch showing in the window, the catheter has its end at the end of the needle.

6. Apparatus as claimed in claim 4 wherein said catheter includes a series of spaced markings along the length of the catheter extending from the proximal end of the coloured patch towards the proximal end of the catheter, each marking being visually distinguishable from the others.

7. Apparatus as claimed in claim 2 wherein the transparent material is a thin-walled tube of heat-shrinkable plastic.

8. Apparatus as claimed in claim 7 wherein the plastic is polytetrafluoethylene.

9. Apparatus for use in accurately locating a catheter with respect to the outer surface of a patient's skin, the apparatus comprising:
    a hollow surgical needle having an elongate stem portion of uniform inner and outer diameters defining a wall terminating in a sharpened leading end and an opening at that end, the stem having a portion of its wall removed to define a longitudinal slot therein, a thin-walled transparent tube being securely fitted over the stem portion, the portion of the tube over the slot defining, with the slot, a window by which the interior of the stem portion can be seen, the window being of sufficient length that when the stem of the needle is inserted into the patient's skin a portion of the window remains outside the skin surface; said tube bonded to said stem to provide airtight separation between an interior of said stem and an exterior of said stem;

a flexible tubular catheter adapted to be slidably inserted in the hollow surgical needle and moveable through the needle to project out beyond said opening in the leading end of the needle, the catheter having a leading end, a coloured patch along its length of the same length as the slot, and a series of different visually distinguishable markings spaced along the catheter from the proximal end of the coloured patch towards the proximal end of the catheter; said patch disposed on said catheter for said catheter leading end to be aligned with said stem leading end when said patch on said catheter is inserted into said needle with said patch filling said window;

whereby, after the needle has been inserted to a required depth the leading end of the catheter can be inserted into and through the needle to a desired position, said desired position being recognized when the coloured patch is aligned with the slot as viewed through the window, and the visually distinguishable markings being used to indicate the amount of catheter subsequently entered into the skin so that, a mark proximal to the proximal end of the coloured patch can be viewed through the window and used as a reference point to permit the catheter to be located in the same position relative to the skin surface after the needle has been removed.

10. Apparatus according to claim 1 wherein said catheter is formed of polytetrafluoroethylene.

11. Apparatus according to claim 9 wherein said catheter is formed of polytetrafluoroethylene.

12. Apparatus according to claim 1 wherein said markings are visually distinctive.

13. A method of inserting a catheter into a peridural space of a patient's spinal area using a hollow surgical needle having an elongate stem with an elongate window formed therein; means for indicating a pressure drop within said needle; a catheter sized to be slidably inserted in said needle and moveable therethrough to project beyond the needle opening, said needle having markings spaced along its length including a first marking cooperating with said window to indicate alignment of a free end of said catheter with said needle opening; said method comprising the steps of:

(a) inserting said needle into said patient with said needle opening directed toward an anticipated site of said peridural space;

(b) advancing said needle opening toward said anticipated site until said means indicates a pressure drop within said needle;

(c) inserting said catheter into said needle and advancing said free end of said catheter toward said needle opening until said first marking and said window cooperate to indicate alignment of said free end with said needle opening;

(d) advancing said free end past said needle opening by a desired amount;

(e) noting a distance between said patient's skin and a selected marking on said catheter;

(f) withdrawing said needle while maintaining said catheter within said patient;

(g) aligning said catheter within said patient until said selected marking is spaced from said skin equal to said noted distance.

* * * * *